United States Patent [19]
Andrade et al.

[11] Patent Number: 4,720,593
[45] Date of Patent: Jan. 19, 1988

[54] PROCESS FOR THE PRODUCTION OF 1-METHYLCYCLOPROPANECARBOX-ALDEHYDE

[75] Inventors: Juan Andrade, Kleinostheim; Gunter Prescher, Hanau; Klaus Kohler, Hainburg, all of Fed. Rep. of Germany

[73] Assignee: Degussa Aktiengesellschaft, Frankfurt am Main, Fed. Rep. of Germany

[21] Appl. No.: 921,473

[22] Filed: Oct. 22, 1986

[30] Foreign Application Priority Data

Oct. 24, 1985 [DE] Fed. Rep. of Germany ....... 3537813

[51] Int. Cl.$^4$ ............................................. C07C 45/65
[52] U.S. Cl. ............................................. 568/420
[58] Field of Search ................. 568/348, 420; 560/124

[56] References Cited

U.S. PATENT DOCUMENTS

| | | | |
|---|---|---|---|
| 3,122,587 | 2/1964 | Stransbury et al. | 560/124 |
| 3,294,833 | 12/1966 | Phillips | 560/124 |
| 4,085,148 | 4/1978 | Cleare | 568/420 |
| 4,195,033 | 3/1980 | Punja | 568/348 |

FOREIGN PATENT DOCUMENTS 2751133  5/1979  Fed. Rep. of Germany ...... 560/124

OTHER PUBLICATIONS

Bartsch et al., J. Org. Chem., vol. 35, #5, pp. 1714–1715 (1970).
Radulescu et al., Chem. Abst., vol. 88, #189,832d (1978).

*Primary Examiner*—James H. Reamer
*Attorney, Agent, or Firm*—Cushman, Darby & Cushman

[57] ABSTRACT

There is disclosed a process for the production of 1-methylcyclopropanecarboxaldehyde of the formula

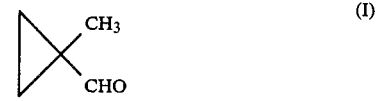
(I)

comprising treating 4-chloro-2-methyl-butanal of the formula

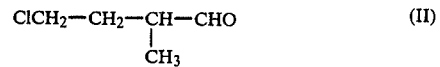
(II)

at a temperature between −40° and +7° C. in an inert solvent with a 1.0 to 10.0 fold molar amount of a strong, non-nucleophilic base.

5 Claims, No Drawings

PROCESS FOR THE PRODUCTION OF 1-METHYLCYCLOPROPANECARBOXALDEHYDE

RELATED CASE

Andrade application (Docket 1426), Ser. No. 921,474 filed on 10/22/86, and corresponding to German patent application P 3537815.8 is directed to preparing the 4-chloro-2-methyl-butanal employed to prepare 1-methylcyclopropanecarboxaldehyde of the present invention. The entire disclosure of the Andrade application is hereby incorporated by reference and relied upon.

BACKGROUND OF THE INVENTION

The invention is directed to a new process for the production of 1-methylcyclopropanecarboxaldehyde of the formula

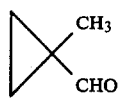
(I)

This cyclopropane derivative is an important starting material for a synthesis of isodehydroabietenolide, which in turn is an intermediate product for the synthesis of the antileukemia agent, triptolide (see J. Amer. Chem. Soc. Vol. 101, pages 7423 (1979)).

It is already known (see J. Org. Chem., Vol. 27, page 51 (1962)) to produce 1-methylcyclopropanecarboxaldehyde by reduction of 1-methylcyclopropanecarbonitrile with lithium aluminum hydride. The 1-methylcyclopropanecarbonitrile in turn can be produced (see J. Amer. Chem. Soc., Vol. 56, page 2710 (1934)) by reaction of methacrylonitrile with diazomethane. However, the conversion with diazomethane is little suited for the production on an industrial scale.

It is already known (J. Amer. Chem. Soc., Vol. 97, page 2778 (1975)) to produce 1-methylcyclopropanecarboxaldehyde by reaction of methallyl alcohol with diiodomethane and dry Zn-Cu-alloy and subsequent oxidation of the 1-methylcyclopropylcarbinol with CrO$_3$ in pyridine. The total yield of 1-methylcyclopropanecarboxaldehyde, however, is low according to this process.

SUMMARY OF THE INVENTION

The present invention is directed to a process for the preparation of 1-methylcyclopropanecarboxaldehyde of the formula

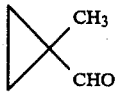
(I)

by treating 4-chloro-2-methyl-butanal of the formula

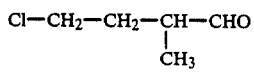
(II)

with a 1.0 to 10.0 fold molar amount of a strong, non-nucleophilic base at a temperature between −40° and +70° C. in an inert solvent.

The treatment with the base is preferably carried out at a temperature between −20° and +20° C. The base is preferably employed in a 1.0 to 4.0 fold molar amount.

The 4-chloro-2-methyl-butanal starting material of formula (II) can be produced for example by reacting 1,1-dimethoxy-2-methyl-4-hydroxy butane with a 1.0 to 10.0 fold molar amount of carbon tetrachloride at a temperature between −20° and +80° C. in the presence of a 0.1 to 20.0 fold molar amount of triphenylphosphine and hydrolyzing in acid medium the 1,1-dimethoxy-2-methyl-4-chloro-butane formed thereby. Suitable inert solvents for the process of the invention, for example, are ethers such as diethyl ether, diisopropyl ether or diethylene glycol dimethyl ether and hydrocarbons such as benzene or decalin.

Suitable strong non-nucleophilic bases for example are alkali hydrides, e.g., sodium hydride, lithium alkyls, e.g., tert. butyl lithium or lithium dialkylamides such as lithium diisopropylamide (and lithium diethylamide, lithium dimethylamide and lithium dibutylamide).

The process of the invention for example can be carried out by suspending the base in the inert solvent and slowly dropping in the 4-chloro-2-methyl-butanal with cooling to a temperature between −40° and +10° C. Then the reaction mixture can be slowly brought to room temperature and optionally for a short time heated to a higher temperature, for example, between 30° and 70° C.

The working up of the crude reaction mixture, for example, can be carried out by slowly dropping in water and cooling until the evolution of gas is ended and then separating off the water phase and discarding it. The organic phase is washed neutral, then, for example, dried over MgSO$_4$ and finally fractionally distilled. Optionally the separation, washing and drying of the organic phase can be eliminated and after ending the addition of water and evolution of gas there can be employed direct fractional distillation. Thereby, however, frequently there occurs a reduction in yield which makes this method of operation less advisable.

The process of the invention can comprise, consist essentially of or consist of the recited steps with the stated materials.

The invention will be explained in more detail in the following examples.

EXAMPLE 1

78.3 grams (0.65 mole) of 4-chloro-2-methyl-butanal were slowly dropped into a suspension of 18.7 grams (0.78 mole) of sodium hydride in 500 ml of absolute ether at +5° C. within 30 minutes. After the end of the addition the reaction mixture was allowed to come to room temperature and then heated for another 2 hours at reflux temperature. Subsequently water was slowly dropped in with cooling, through which an exothermic reaction set in with the development of gas. After the end of the development of gas the aqueous phase was separated off and discarded. The organic phase was washed several times with water and then dried over MgSO$_4$. The MgSO$_4$ was filtered off, the organic phase was concentrated at normal pressure over a Vigreux column and the residue fractionally distilled at 125 mbar.

The 1-methylcyclopropanecarboxaldehyde passed over at 50° to 52° C. The yield was 27 grams (49.2% of theory).

EXAMPLE 2

25 grams (0.21 mole) of 4-chloro-2-methylbutanal were slowly dropped into a suspension of 50 grams (0.46 mole) of lithium diisopropylamide in 200 ml of absolute diethyl ether at −25° C. within 30 minutes. After the end of the addition, the reaction mixture was allowed to come to room temperature and then heated for one hour more at reflux temperature. Subsequently water was slowly dropped in with cooling. The organic phase was separated off, washed with 5 weight percent hydrochloric acid, then with sodium carbonate solution and finally with water and further processed as in Example 1.

The yield of 1-methylcyclopropanecarboxaldehyde was 11.8 grams (67.6% of theory).

EXAMPLE 3

60.3 grams (0.5 mole) of 4-chloro-2-methylbutanal were slowly dropped into a suspension of 12 grams (0.5 mole) of sodium hydride in 250 ml of diethylene glycol dimethyl ether at 0° C. The reaction mixture was allowed to come to room temperature and heated for 2 more hours at 60° C. Subsequently it was fractionally distilled directly at normal pressure over a Vigreux column.

The 1-methylcyclopropanecarboxaldehyde passed over at 103° to 107° C. The yield was 14.2 grams (33.8% of theory).

EXAMPLE 4

24.1 grams (0.2 mole) of 4-chloro-2-methylbutanal were dropped into a suspension of 16 grams (0.67 mole) of sodium hydride in 150 ml of benzene at 0° C. within one hour. After the end of the addition the reaction mixture was allowed to come to room temperature and heated for a further 2 hours at 80° C. The working up was carried out as in Example 1.

The yield of 1-methylcyclopropanecarboxaldehyde was 9.2 grams (55.0% of theory).

EXAMPLE 5

12 grams (0.1 mole) of 4-chloro-2-methylbutanal were slowly dropped into 90 grams (0.2 mole) of a 15 weight percent solution of tert butyl lithium in a pentane/hexane mixture at −10° C. After the end of the addition the reaction mixture was allowed to come to room temperature and then heated for a further 2 hours at reflux temperature. The further processing was carried out as in Example 1.

The yield of 1-methylcyclopropanecarboxaldehyde was 5.2 grams (62.0% of theory).

The entire disclosure of German priority application P 3537813.1 is hereby incorporated by reference.

It is claimed:

1. A process for the production of 1-methylcyclopropanecarboxaldehyde of the formula

comprising treating 4-chloro-2-methyl butanal of the formula

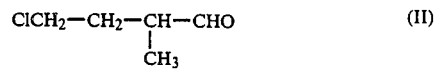

in an inert solvent with a 1.0 to 10.0 fold molar amount of a strong non-nucleophilic base at a temperature between −40° and +70° C.

2. A process according to claim 1 wherein the treatment with the base is at a temperature between −20° and +20° C.

3. A process according to claim 2 wherein the base is employed in a 1.0 to 4.0 fold molar amount of the 4-chloro-2-methyl butanal.

4. A process according to claim 1 wherein the base is employed in a 1.0 to 4.0 fold molar amount of the 4-chloro-2-methyl butanal.

5. A process according to claim 1 wherein the non-nucleophilic base is an alkali metal hydride, a lithium alkyl or a lithium dialkylamide.

* * * * *